US009874821B2

(12) United States Patent
Halder et al.

(10) Patent No.: US 9,874,821 B2
(45) Date of Patent: Jan. 23, 2018

(54) METHOD FOR HOTSPOT DETECTION AND RANKING OF A LITHOGRAPHIC MASK

(71) Applicant: IMEC VZW, Leuven (BE)

(72) Inventors: Sandip Halder, Heverlee (BE); Dieter Van Den Heuvel, Westerloo (BE); Vincent Truffert, Vorst (BE); Philippe Leray, Terhulpen (BE)

(73) Assignee: IMEC VZW, Leuven (BE)

( * ) Notice: Subject to any disclaimer, the term of this patent is extended or adjusted under 35 U.S.C. 154(b) by 119 days.

(21) Appl. No.: 15/134,616

(22) Filed: Apr. 21, 2016

(65) Prior Publication Data
US 2016/0313647 A1   Oct. 27, 2016

(30) Foreign Application Priority Data

Apr. 22, 2015  (EP) .................................... 15164693

(51) Int. Cl.
*G01N 21/00*   (2006.01)
*G03F 7/20*   (2006.01)
(Continued)

(52) U.S. Cl.
CPC ....... *G03F 7/7065* (2013.01); *G01N 21/8851* (2013.01); *G01N 21/95607* (2013.01); *G03F 1/84* (2013.01); *G03F 7/70441* (2013.01); *G03F 7/70625* (2013.01); *G03F 7/70641* (2013.01); *G01N 2021/8854* (2013.01); *G01N 2021/95676* (2013.01)

(58) Field of Classification Search
CPC ............. G01N 21/8851; G01N 21/956; G01N 21/95676; G01N 21/95607; G01N 2021/8854; G03F 1/84; G03F 7/7065

USPC .......... 356/237.1–237.5; 382/144, 145, 147, 382/149
See application file for complete search history.

(56) References Cited

U.S. PATENT DOCUMENTS 7,119,893 B2   10/2006 Littau et al.
7,729,529 B2   6/2010 Wu et al.
(Continued)

FOREIGN PATENT DOCUMENTS

WO   2006/063268 A2   6/2006
WO   2013/029957 A2   3/2013

OTHER PUBLICATIONS

Ausschnitt, Christopher P. et al., "Modeling for Profile-Based Process-Window Metrology", Proc. of SPIE, vol. 5378, Apr. 29, 2004, pp. 38-47.
(Continued)

*Primary Examiner* — Hoa Pham
(74) *Attorney, Agent, or Firm* — McDonnell Boehnen Hulbert & Berghoff LLP

(57) ABSTRACT

The present disclosure is related to a method for detecting and ranking hotspots in a lithographic mask used for printing a pattern on a substrate. According to example embodiments, the ranking is based on defect detection on a modulated focus wafer or a modulated dose wafer, where the actual de-focus or dose value at defect locations is taken into account, in addition to a de-focus or dose setting applied to a lithographic tool when a mask pattern is printed on the wafer. Additionally or alternatively, lithographic parameters other than the de-focus or dose can be used as a basis for the ranking method.

8 Claims, 3 Drawing Sheets

(51) Int. Cl.
*G03F 1/84* (2012.01)
*G01N 21/88* (2006.01)
*G01N 21/956* (2006.01)

(56) References Cited

U.S. PATENT DOCUMENTS

| | | |
|---|---|---|
| 7,749,666 B2 | 7/2010 | Gassner et al. |
| 7,783,104 B2 | 8/2010 | Kawaragi |
| 7,941,232 B2 | 5/2011 | Ishii et al. |
| 2006/0273266 A1 | 12/2006 | Preil et al. |
| 2007/0035728 A1 | 2/2007 | Kekare et al. |
| 2007/0156379 A1* | 7/2007 | Kulkarni ............ G06F 17/5045 703/14 |
| 2007/0288219 A1* | 12/2007 | Zafar ................ G03F 1/84 703/14 |
| 2014/0199792 A1* | 7/2014 | Miyoshi ............ H01L 22/12 438/16 |
| 2015/0029499 A1 | 1/2015 | Wright et al. |
| 2015/0254832 A1* | 9/2015 | Plihal ................ G06T 7/001 382/149 |
| 2016/0123898 A1* | 5/2016 | Chen ................ G01N 21/9501 356/237.5 |
| 2016/0150191 A1* | 5/2016 | Karsenti ............ H04N 7/181 382/149 |
| 2017/0167992 A1* | 6/2017 | Halder ............... G01N 23/2251 |

OTHER PUBLICATIONS

Hinnen, Paul et al., "Scatterometry-Based On-Product Focus Measurement and Monitoring", ASMC 2013 Semi Advanced Semiconductor Manufacturing Conference, May 14-16, 2013, pp. 352-359.
European Search Report, European Patent Application No. 15164693.2, dated Oct. 26, 2015.
Hunsche, Stefan et al., "A New Paradigm for In-Line Detection and Control of Patterning Defects", Proceedings of SPIE, S P I E—International Society for Optical Engineering, vol. 9424, Mar. 19, 2015, pp. 1-12.

* cited by examiner

METHOD FOR HOTSPOT DETECTION AND RANKING OF A LITHOGRAPHIC MASK

CROSS-REFERENCE TO RELATED APPLICATION

The present application is a non-provisional patent application claiming priority to European Patent Application No. 15164693.2 filed Apr. 22, 2015, the contents of which are hereby incorporated by reference.

TECHNICAL FIELD

The present disclosure is related to the detection and ranking of potential error locations, referred to as hotspots, in the design of lithographic masks used for the production of semiconductor devices.

BACKGROUND

A semiconductor device, such as an integrated circuit chip, is produced by a sequence of hundreds of process steps, many of which require a lithographic mask through which a design pattern is imprinted on a photoresist layer. So-called hotspots of a design pattern are the areas which are likely to be printed incorrectly due, for example, to certain geometrical parameters of the design and their interaction with optical phenomena taking place during the exposure of the mask. Many of the hotspots can be predicted and solved by design software, such as litho pattern simulation software and OPC (Optical Proximity Correction) software. However, it is not possible to predict all possible defects, which makes it necessary to apply actual defect detection on a printed wafer.

An important factor in the appearance of defects on a printed wafer is the quality of focus of the lithographic tool used in the device manufacturing process. This quality of focus is expressed as a tolerance with respect to perfect focus (i.e. zero de-focus), expressed, for example, as a range of de-focus values on either side of the zero de-focus state. For example, a lithographic tool may have a focus tolerance of [−40 nm, +40 nm], meaning that the focus may unpredictably vary within this range due to inaccuracies in the tool, wear of the tool, environmental changes, etc.

Many hotspots identified on a mask design defining a given pattern do not appear as actual defects in the printed pattern unless the defocus of the lithography tool exceeds a given limit value. For this reason, it is customary to make a ranking of defects based on their sensitivity to the degree of de-focus. Defects appearing at the lowest de-focus values are ranked highest. These defects are likely to occur in a production process where the tolerance of the focus is higher than the focus error at which the defects occur. For example, a defect occurring at +10 nm de-focus is likely to occur when using a tool with the above-described tolerance of [−40 nm, +40 nm]. Hence these hotspots are most critical and most in need of correction.

In order to make the ranking, the so-called modulated focus wafer technique may be used, in which a pattern is printed multiple times on a wafer, on multiple separate semiconductor die areas of the wafer, with the focus changing in steps of, for example, +/−10 nm, from zero de-focus to gradually more out-of-focus values. Each printed die area is then inspected, and where repeating defects are detected, i.e., defects appearing in successively more de-focused prints, these hotspots are ranked in the above-described way. One example of this approach is shown in WO/2006/063268.

As the dimensions of printed features decreases with the evolution towards sub 32 nm nodes in semiconductor processing, the criticality of the above-described design and inspection processes becomes ever greater. One problem is that the modulated focus wafer technique assumes that a uniform focus applies to the totality of the printed surface of a particular die, but fails to take into account focus variations within each die. When these variations approach values that are in the same order of magnitude as the incremental steps used in the test procedure, ranking errors are likely to occur.

SUMMARY OF THE DISCLOSURE

The present disclosure is related to a method, as recited in the appended claims, for detecting and ranking hotspots in a lithographic mask used for printing a pattern on a substrate. According to example embodiments, the ranking is based on defect detection on a modulated focus wafer or a modulated dose wafer, where the actual de-focus or dose value at the defect locations is taken into account in addition to the de-focus or dose setting applied to the lithographic tool when a mask pattern is printed on the wafer.

The present disclosure is thus related to a method for detecting and ranking hotspots in a lithographic mask for printing a pattern on a substrate. An example method may include the steps of: providing a test substrate comprising a plurality of die areas; printing the pattern through the mask on the plurality of die areas with a lithographic tool, where a lithographic parameter of the tool is incremented, starting from a set value of the parameter at one of the die areas, and increasing and/or decreasing the parameter stepwise in at least a portion of the other die areas, i.e., in at least some of the other die areas, with the set parameter being increased or decreased when passing from one die area to another; examining each of the die areas for defects and recording one or more repeating defects, defined as defects which occur starting from a first value of the parameter and which are repeated for at least one second value of the parameter, the locations where repeating defects occur being defined as hotspots; determining for each individual repeating defect in each of the die areas, the actual local parameter value at the location of the defect; and ranking the hotspots, the ranking being determined by whether a defect detected at the hotspot location is a repeating defect and by the actual local parameter values at the locations (i.e., at multiple dies printed at different set parameter values) at which the defect is detected. This means that hotspots are ranked according to the value of the actual local parameter.

According to an example embodiment, when the "set" value of the parameter is increased or decreased starting from an initial value, such as zero, the defect that first appears while corresponding to the lowest absolute value of the local parameter compared to other defects, is attributed the highest position in the ranking. For parameters with both positive and negative values, such as the de-focus value, a separate ranking may be made for parameter values from zero and upwards and for parameter values from zero and downwards.

The term "detecting" refers to the "recording of one or more repeating defects." Hotspot locations could actually be detected for the first time during the "examining" stage of the method of the disclosure. Alternatively, the hotspot locations themselves are defined previously during the design stage of the mask, for example by an optical proximity correction (OPC) tool. The disclosure presents a novel way of ranking these hotspots as a function of one or more lithography parameters in order to identify the most critical hotspots. These most critical hotspots can then be further analyzed and modeled by extensive experiments, such as those described in "A new paradigm for in-line detection and control of patterning defects," Hunsche et al., Proc. of SPIE, Vol. 9424, p. 94241B-1 to 94241B-8.

According to an example embodiment, the set value of the parameter is a set value of the de-focus setting for the lithographic tool, the set value being referred to as zero average de-focus and the actual value of the parameter being the actual de-focus value at the defect location, so that a hotspot is ranked highest when it is detected as a defect at the lowest absolute value of the actual de-focus value.

The step of determining the actual de-focus value at the location of a defect may include: determining or estimating the positive or negative distance between the plane corresponding to zero average de-focus and the local zero de-focus plane for the defect, and adding the distance to the average de-focus value applied to the tool when printing the defect. The distance may be determined on the basis of a focus map for the entire substrate, or it may be determined only at the defect locations.

A de-focus value is said to be higher than another de-focus value if its absolute value is higher than the other value's absolute value. For example, +50 nm is a higher de-focus value than +40 nm as well as −40 nm; −60 nm is a higher de-focus value than +30 nm.

According to an example embodiment, the set value of the parameter is a set value for the dose setting of the lithographic tool, and the actual value of the parameter is the actual value of the dose applied to a defect location. The actual dose may be determined on the basis of a dose map for the entire substrate, or it may be determined only at the defect locations.

DETAILED DESCRIPTION

Figure 1:
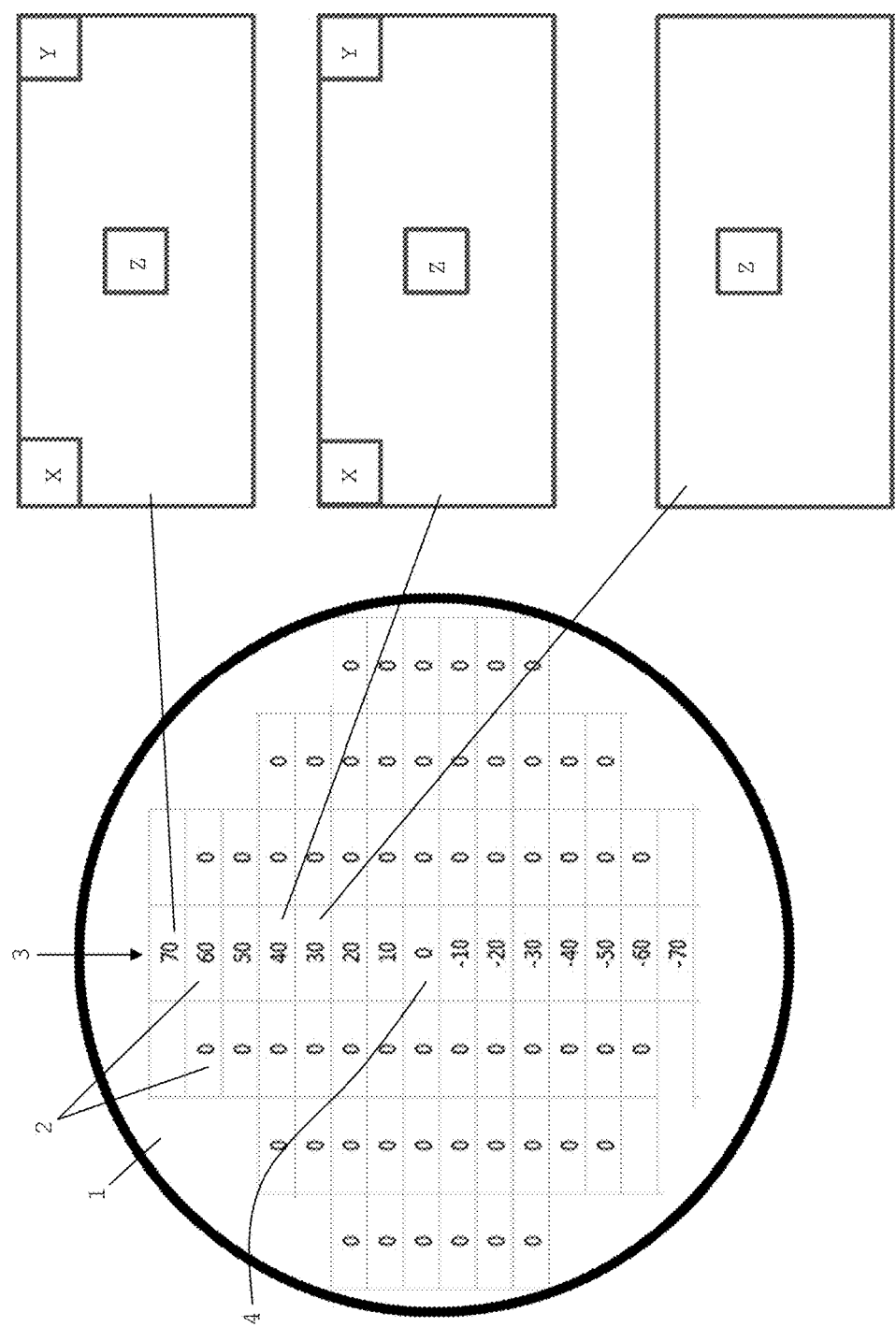
FIG. 1 illustrates a test wafer and shows details of three die areas corresponding to different values of the average de-focus values used for printing these areas, also indicating a number of defect locations.

FIG. 1 illustrates the above-described ranking problem on the basis of a concrete example. A test wafer 1 is shown, comprising a plurality of die areas 2 arranged in rows and columns. The central column of dies is a modulated focus column 3. The modulated focus column 3 represents die areas 2 where a particular pattern is printed with incrementally changing de-focus values deliberately applied in the lithographic printing tool, when the pattern is printed in these areas. The de-focus values are shown on the dies 2 of the modulated focus column 3, and are expressed in nanometers (nm). The term "printing" of the pattern is to be understood as comprising an exposure of a resist layer applied on the test wafer, through the litho-mask, and developing the resist layer so that the exposed areas of the resist become visibly distinct from non-exposed areas. The lithography tool can be any suitable known type of tool, such as a wafer stepper or a wafer scanner, where a pulsed laser beam is scanned through the mask and through a suitable lens assembly, illuminating portions of a die area as defined by the mask's pattern.

The central die 4 represents the zero de-focus position of the lithographic mask with respect to the wafer 1, i.e., the best obtainable in-focus print of the die. This does not mean that every point of the central die 4 is perfectly in focus. Necessarily, the zero de-focus position is an approximation based, for example, on the printing and analysis of a Focus Exposure energy Matrix (FEM) wafer. The FEM approach is known as such for obtaining the optimal set values for the focus as well as the exposure energy (hereafter called 'dose') when printing a pattern, based on measurements of the critical dimension (CD) of features in the pattern.

As stated, the use of the optimal defocus value derived from this procedure does not mean that every feature in the printed pattern is perfectly in focus. The central die 4 of the test wafer shown in FIG. 1 is therefore referred to as the die printed at an "average" de-focus value of zero. The term "average" does not, however, imply that the zero-de-focus condition used for printing the central die is a mathematical average of other de-focus values. An alternative name for "average" defocus could be "set" de-focus or "nominal" de-focus.

Above and underneath the central die, de-focused prints are produced at incrementally increasing average de-focus values on either side of the zero value, in steps of +10 nm and −10 nm, obtained by displacing the lens assembly of the litho-tool in incremental steps with respect to the zero de-focus position.

The rest of the dies 2 in the wafer 1 (outside the central column 3) are illustrated as average zero-defocus dies, but could also be additional de-focused prints. In some examples, a zero-defocused column may be printed next to a modulated focus column in order to facilitate the detection of defects by comparison of two adjacent dies.

Enlarged views are shown of the printed dies at average de-focus values of +30 nm, +40 nm, and +70 nm. It is assumed that no repeating defects are detected in the prints produced at zero, +10 nm, and +20 nm. In the +30 nm print, one defect is detected, illustrated by a square labeled "Z." In other words, the defect does not occur unless the lithographic tool is out of focus at a value between 20 nm and 30 nm in the positive direction. So when the de-focus value increases above 30 nm, defect Z appears again, as shown in the prints at +40 nm and +70 nm. Defects X and Y appear starting from +40 nm.

The ranking of these defects in current practice yields the following results:
Rank 1—defect Z; and
Rank 2—defects X and Y.
This ranking relies on the assumption that the "nominal" or "set" de-focus values applied in the consecutive prints, i.e., 0, +10 nm, +20 nm, etc., represent the actual de-focus value at every defect location. As stated above, this assumption is actually incorrect, given that the nominal de-focus values do not necessarily represent the exact degree of (de)focus on every location within the die area.

Figure 2:
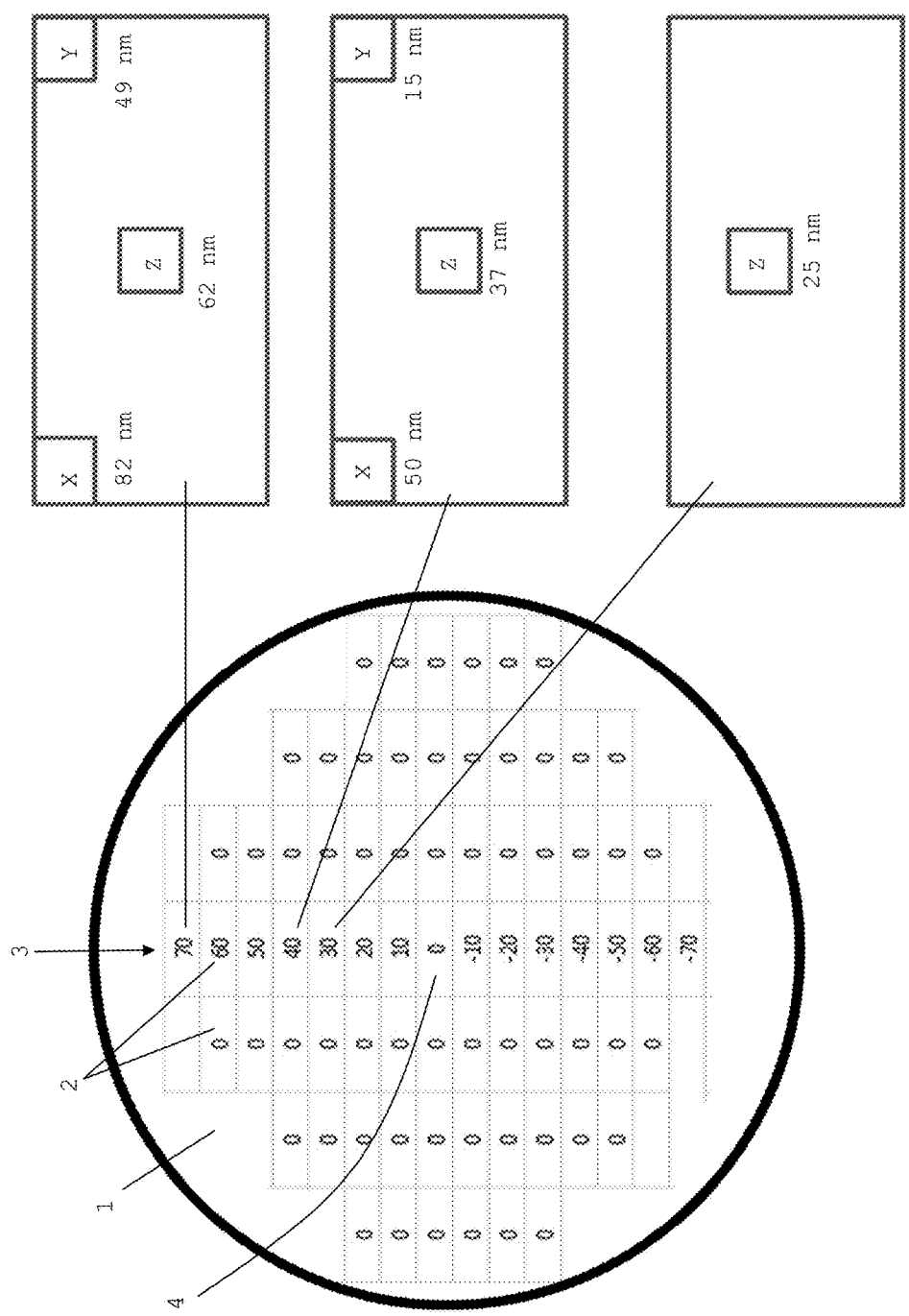
FIG. 2 illustrates the same test wafer and the same die areas, further indicating the actual de-focus values at each of the defect locations.

The present disclosure is distinct from the above-described ranking procedure by taking into account intra-die focus variations within the surface of each printed die. FIG. 2 shows the same three dies at average de-focus values of +30 nm, +40 nm and +70 nm as in FIG. 1. This time, however, the local actual de-focus value at each of the defect locations is taken into account. These values are printed next to the defect locations in each of the three dies. Now it becomes clear that in the +40 nm die, defect Y is actually printed at a de-focus value of +15 nm instead of +40 nm. This may be due to local unevenness of the wafer surface for example. The local defocus value of defect Z in the +30 nm die is +25 nm, i.e., higher than defect Y in the +40 nm die.

This illustrates that local variations of the de-focus values may be in the same order of magnitude as the nominal average de-focus values applied to the consecutive dies in the test wafer. As a consequence, the ranking of the defects may be influenced. Defect Y appears at the lowest actual de-focus value of +15 nm and higher, followed by defect Z at +25 nm and higher, followed by defect X at +50 nm and higher. The correct ranking is, therefore:

Rank 1—defect Y;
Rank 2—defect Z; and
Rank 3—defect X.

The detection of defects as such can take place according to any known method, for example using e-beam or optical inspection of the printed die, where a de-focused die is compared to a zero de-focus die located adjacent to it.

The determination of the actual de-focus value at the defect locations may include the steps of: determining or estimating the positive or negative distance between the focus plane corresponding to average zero de-focus (e.g., the central die 4 in the test wafer 1) and the local zero de-focus plane for each defect, and adding the distance to the average de-focus value in the die areas where the defects are found The distance referred to above can be determined for a complete test wafer, by measuring a focus map of the complete wafer. A focus map may be obtained by including a number of focus-sensitive features inside and/or around each of the die areas 2 on the test wafer. "Focus-sensitive" means that an identifiable relationship (for example a linear relationship) exists between a measurable quantity of the feature and the local de-focus value at the location of the feature. Such a relationship may be determined, for example, by producing and measuring multiple prints of the focus-sensitive feature on a FEM wafer.

By measuring the measurable quantity on the test wafer 1 of FIG. 1, for example by a scatterometry measurement, the local (as opposed to average) de-focus values at the positions of the focus-sensitive features on the test wafer can be determined. Local de-focus values refer to the position of the local zero-defocus plane at the location of the focus-sensitive target, with respect to the average zero defocus plane. From these local de-focus values at the positions of the focus sensitive features, the de-focus values at other locations within each die area can then be determined by suitable interpolation algorithms, resulting in a focus map for the complete test wafer. An example of a procedure for determining a focus map is described in "Scatterometry-based on-product focus measurement and monitoring," P. Hinnen et al., proceedings ASMC2013, p. 352-359.

Another reference that discloses a method for determining a focus map, referred to as a "hybrid dense focus map" (HDFM) is the previously cited "A new paradigm for in-line detection and control of patterning defects," by Hunsche et al. This reference relies on local focus variations for creating a defect prediction model for particular defects, based on a large number of SEM images of the defect (6000 in the described experiment), and quantification of the defect by area measurements of the particular device pattern at the hotspot location. The initial identification of the most critical hotspot locations in this study is, however, not based on local focus variations, but on a Lithography Manufacturability Check (LMC), which is a method based on a simulation of the lithography process, or on the Process Window Qualification technique (PWQ). PWQ is the prior art technique described above with reference to FIG. 1, where defects are ranked according to the "set" focus values applied on a plurality of prints printed on a Focus Exposure Matrix (FEM) wafer.

By combining the focus map with the detected location of defects in the printed test wafer 1, it becomes possible to determine, or at least estimate, the local de-focus values at the defect locations X, Y, and Z in every die of the modulated focus column 3. The resolution of the focus map can be chosen so as to correspond with the average defect size, or to allow determination of the defocus value at a defect by averaging a limited number of local de-focus values obtained from the focus map.

Adding the local de-focus value at a defect location to the average de-focus value applied in the die area where the defect is found yields the actual de-focus value of the defect (e.g., the numbers indicated in FIG. 2 next to the defect locations).

The creation of a focus map is not the only way of obtaining the local de-focus values. Alternatively, the actual de-focus values may be determined only on those locations where defects are found. This may be done by a measurement of the critical dimensions of well-defined features at the defect location by Scanning Electron Microscopy (SEM). If a pre-defined relationship is known between the measured CD value and the de-focus value, the local de-focus value at the defect location can be determined. The ranking is based on the absolute value of the actual de-focus values. For example, a defect appearing at an actual de-focus value of −5 nm would be ranked higher than a defect appearing at an actual de-focus value of +10 nm.

The present disclosure is not only related to a method for ranking hotspots based on intra-die focus variations, but also to a method for ranking hotspots based on intra-die dose variations. As stated above, the dose refers to the exposure energy supplied to a printed wafer during exposure through the lithographic mask. The dose is most commonly expressed as a value in $mJ/cm^2$.

The optimal dose setting of the litho-tool can be derived from the same FEM wafer technique referred to above, resulting in an optimized "average" dose, i.e., the dose setting chosen for the lithographic tool when printing a pattern. However, due to a variety of effects, e.g., alignment and/or wafer positioning errors, the actual dose applied to each location within a die area is not necessarily equal to this average dose value. The ranking of hotspots based on the average dose is known in the art and takes place in an analogous way as the ranking based on average focus, described with respect to FIGS. 1 and 2.

Figure 3:
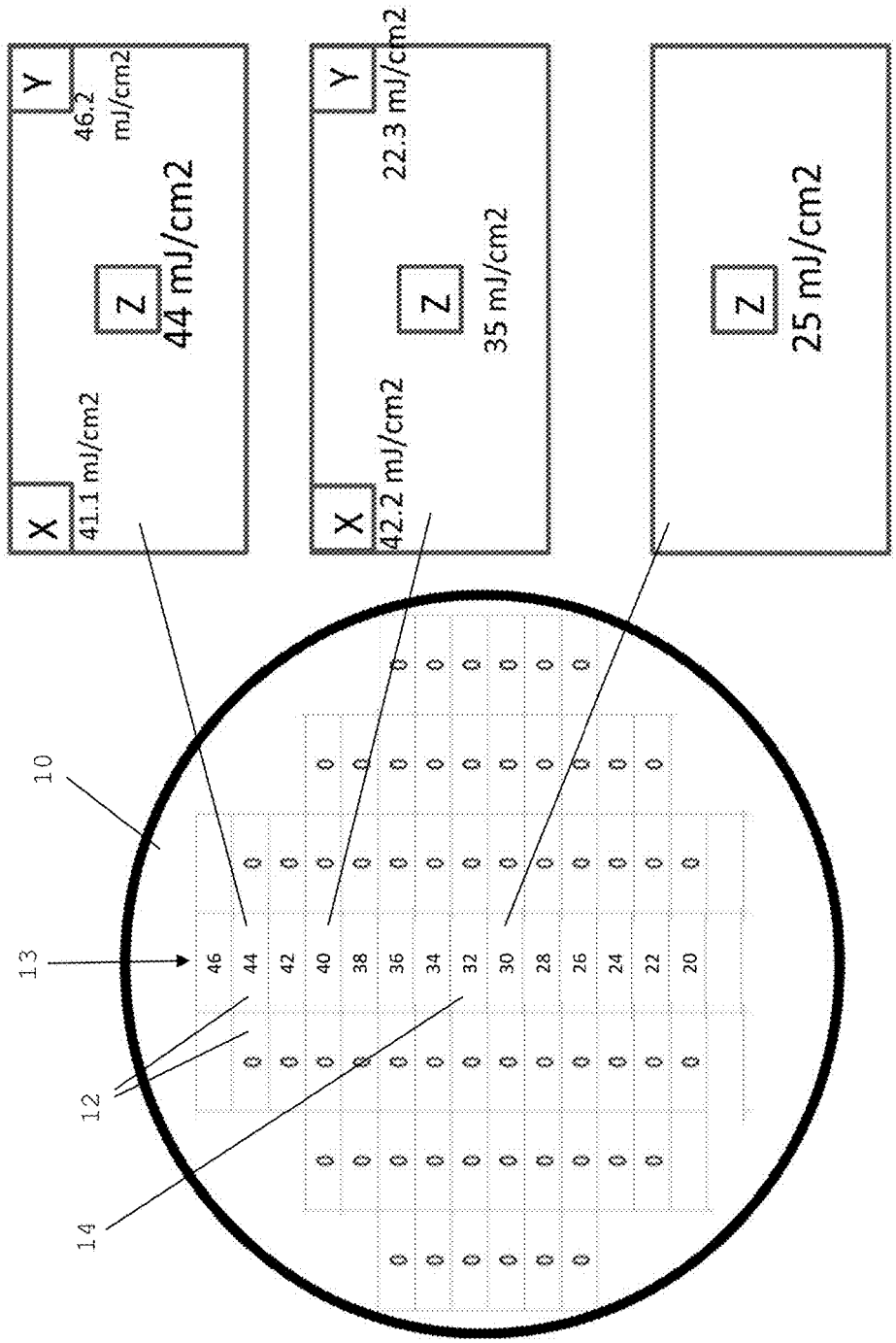
FIG. 3 illustrates a test wafer for ranking hotspots according to an example embodiment.

FIG. 3 illustrates a test wafer 10 comprising rows and columns of die areas 12, similarly to the wafer of FIGS. 1 and 2, where the central column 13 is a modulated dose column. The central die area 14 is printed with "average" dose 32 $mJ/cm^2$, e.g., the value obtained as the optimal dose after a FEM measurement, for example. The other dies in the central column 13 are printed at incrementally increasing and decreasing dose values, as shown by the values indicated in FIG. 3. Then, the defect detection is done in the same way as described with respect to the focus modulated wafer. In some examples, and not as shown in FIG. 3, at least one column adjacent to the central column 14 may be printed in each die with the optimal dose of 32 $mJ/cm^2$, so that adjacent dies can be compared for defect detection. Again, three dies are shown in more detail, corresponding respectively to average doses of 30 $mJ/cm^2$, 40 $mJ/cm^2$, and 44 mJ/cm$^2$, with defects Z, X, and Y appearing. The ranking of these defects based on the average dose would be:

Rank 1—Z (appearing at 30 mJ/cm$^2$ and higher); and

Rank 2—X and Y (appearing at 40 mJ/cm$^2$ and higher).

The ranking made according to the method of the present disclosure takes into account the actual dose values applied to the defect locations. These values are indicated also in FIG. 3. Based on these values, the ranking is:

Rank 1—Y (appears at actual dose of 22.3 mJ/cm$^2$ and higher);

Rank 2—Z (appears at actual dose of 25 mJ/cm$^2$ and higher); and

Rank 3—X (appears at actual dose of 41.1 mJ/cm$^2$ and higher).

The actual dose value at the defect locations can be derived from a dose map of the test wafer. It is equally well known in the art to determine a dose map of a wafer as it is to determine a focus map. Similar to the focus map, the dose map is obtainable by providing dose-sensitive features in or around the die areas on the test wafer, and determining, based on, for example, a scatterometry measurement, the actual dose applied at a plurality of locations across the test wafer. A reference related to the measurement of a dose map as well as a focus map is "Modelling for profile-based process-window metrology," Ausschnitt et al., Proceedings of SPIE 2004, Vol. 5378, p. 38-47.

Alternatively, the actual dose may be determined only at the locations of the defects detected in the die areas of the test wafer 10, for example by a CD-SEM measurement at the defect locations.

It is possible to use a single wafer for making the focus-based ranking and the dose-based ranking by producing a focus modulated column and a dose modulated column on the same wafer.

In some examples, when the average de-focus value is modulated when printing the dies in the focus modulated column 3 (FIGS. 1 and 2), the average dose (i.e., the set value for the dose) is kept constant. Only when the focus-sensitive features are very insensitive to dose variations may a variation for the dose set value be allowed. Likewise, when the average dose is modulated when printing the dies in the dose modulated column 13, the average focus may be kept constant, except when the dose-sensitive features are exceedingly insensitive to focus variations.

In addition to the de-focus and dose, other lithographic parameters, such as parameters related to overlay or aberration effects, could be used as a basis for making the ranking, provided that there is a distinction between a set value of the parameter and the actual value of the parameter at the location of a defect. The methodology for producing such a ranking is completely analogous to the methods described above in relation to focus modulated and dose modulated wafers 1, 10, including the methods for producing a "parameter map" of a modulated parameter test wafer.

While the present disclosure has been illustrated and described in detail in the drawings and foregoing description, such illustration and description are to be considered illustrative and not restrictive. Other variations to the disclosed embodiments can be understood and effected by those skilled in the art in practicing the claimed disclosure, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

What is claimed is:

1. A method for detecting and ranking hotspots in a lithographic mask for printing a pattern on a substrate, the method comprising:
   providing a test substrate comprising a plurality of die areas;
   printing the pattern through the mask on the plurality of die areas with a lithographic tool, wherein printing the pattern includes incrementing a lithographic parameter of the tool from an initial set value of the parameter used when printing the pattern on one of the die areas to one or more other set values of the parameter used when printing the pattern on others of the die areas, and wherein incrementing the parameter comprises increasing or decreasing the set value of the parameter stepwise;
   determining a location of one or more repeating defects, wherein the repeating defects occur at a first die area associated with a first set value of the parameter and at a second die area associated with a second set value of the parameter;
   determining for each of the one or more repeating defects an actual parameter value associated with a location of the defect; and
   ranking the defects based on whether each defect is a repeating defect and based on the actual parameter values.

2. The method according to claim 1, wherein each of the set values of the parameter is a set value of a de-focus setting for the lithographic tool, and wherein the actual parameter value is an actual de-focus value of the tool when printing the pattern at the defect location, and wherein a defect is ranked highest when it is associated with a lowest absolute value of the actual de-focus value.

3. The method according to claim 2, wherein determining the actual de-focus value of the tool when printing the pattern at the location of the defect comprises:
   determining a positive or negative distance between a plane corresponding to a zero average de-focus value associated with the die area in which the defect is located and a local zero de-focus plane associated with the location of the defect; and
   adding the determined distance to the set value of the de-focus setting for the lithographic tool used when printing the pattern on the die area in which the defect is located.

4. The method according to claim 3, wherein the distance is determined based on a focus map for the entire substrate.

5. The method according to claim 3, wherein the distance is determined only at the defect locations.

6. The method according to claim 1, wherein the set value of the parameter is a set value for a dose setting of the lithographic tool, and wherein the actual parameter value is an actual value of the dose applied to the defect location.

7. The method according to claim 6, wherein the actual dose is determined based on a dose map for the entire substrate.

8. The method according to claim 6, wherein the actual dose is determined only at the defect locations.

* * * * *